US00PP26527P2

(12) United States Plant Patent
Ramming et al.

(10) Patent No.: US PP26,527 P2
(45) Date of Patent: Mar. 22, 2016

(54) GRAPEVINE DENOMINATED 'SUNPREME'

(50) Latin Name: ***Vitis vinifera* L.**
Varietal Denomination: Sunpreme

(71) Applicant: The United States of America, as represented by the Secretary of Agriculture, Washington, DC (US)

(72) Inventors: David W Ramming, Fresno, CA (US); Ronald E Tarailo, Fresno, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 191 days.

(21) Appl. No.: 13/998,571

(22) Filed: Nov. 12, 2013

(51) Int. Cl.
*A01H 5/08* (2006.01)

(52) U.S. Cl.
USPC ..... Plt./205

(58) Field of Classification Search
USPC ..... Plt./207, 205
See application file for complete search history.

(56) References Cited

U.S. PATENT DOCUMENTS

| | | | |
|---|---|---|---|
| PP2,961 | P | 1/1970 | Gebhart |
| PP3,295 | P | 1/1973 | Garabedian |
| PP4,077 | P | 7/1977 | Anderson |
| PP4,784 | P | 11/1981 | Olmo et al. |
| PP4,873 | P | 8/1982 | Corrin |
| PP5,833 | P | 12/1986 | Gargiulo |
| PP13,607 | P2 | 2/2003 | Asadoorian |

*Primary Examiner* — Susan McCormick Ewoldt
(74) *Attorney, Agent, or Firm* — John D. Fado; Gail E. Poulos; Lesley Shaw

(57) ABSTRACT

The present invention relates to a new and distinct variety of grapevine, *Vitis vinifera* L., which will be denominated varietally as the 'Sunpreme' grapevine. The new and distinct 'Sunpreme' grapevine variety is characterized by the production of medium-sized green-colored seedless berries that begin to wilt naturally during mid-July in the San Joaquin Valley of Central California. The noted berry wilting is the first step in raisining, after which berries begin to brown naturally on the vine. The dried grapes (raisins) of this new variety are produced on strong woody canes that do not need to be cut from the mother vine to facilitate berry drying.

5 Drawing Sheets

Latin name of the genus and species of the plant claimed: 'Sunpreme' is a new grapevine plant that is *Vitis vinifera* L.

Variety denomination: The new grapevine plant claimed is of the variety denominated 'Sunpreme.'

BACKGROUND OF THE INVENTION

The present invention is to a new and distinct grapevine plant designated 'Sunpreme' and botanically known as *Vitis vinifera* L. This new grapevine is the result of hybridization between A4-162 (seeded mother vine) and C82-88 (seedless pollen parent), both parents being unpatented. The original vine was planted in a field plot in Fresno, Calif. The new variety has been tested as selection B82-43 at Fresno and at Parlier in the San Joaquin Valley of California.

This new and distinct variety of grapevine produces white-skinned seedless berries of the stenospermic type that dehydrate naturally on the vine to produce raisins. The natural raisining of grape berries of the present invention typically occurs during the month of August, allowing for an early harvest as compared with tray-dried raisins of variety 'Thompson Seedless' in the San Joaquin Valley of Central California.

The 'Sunpreme' grapevine is characterized by producing medium-sized, white-skinned seedless berries that raisin naturally on the vine without cutting of fruit-bearing canes. The berries dehydrate to a state ready for harvest early in the season as compared with the harvest pick-up date of traditional tray-dried 'Thompson Seedless.' 'Sunpreme' grapevines set a full crop of grape clusters when spur-pruned, as compared with very limited production of 'Thompson Seedless' when pruned in a similar manner.

The new variety is distinguished from its seed parent, A4-162, in that the new variety has seedless berries with white skin, whereas A4-162 produces red-skinned berries with viable seed. Clear differences in berry skin color also distinguish the new variety (berry skin color is white) from pollen parent C82-88 (berry skin color is red).

During 2001, dormant cuttings of the new variety were taken from the mother vine in the Fresno vineyard for clonal propagation and advanced testing in Parlier, Calif. Rooted cuttings of the present invention were planted and allowed to establish at the advanced testing site. All propagated vines arising from the original mother plant have been observed to be true-to-type, with both vegetative and fruit characteristics of the original plant being maintained through propagation.

BRIEF DESCRIPTION OF THE DRAWINGS

The accompanying color photographs of FIGS. 1, 2, 4 and 5 show typical specimen of the new cultivar at various stages of development as nearly true as it is possible to make in color reproductions.

DETAILED BOTANICAL DESCRIPTION

Figure 1:
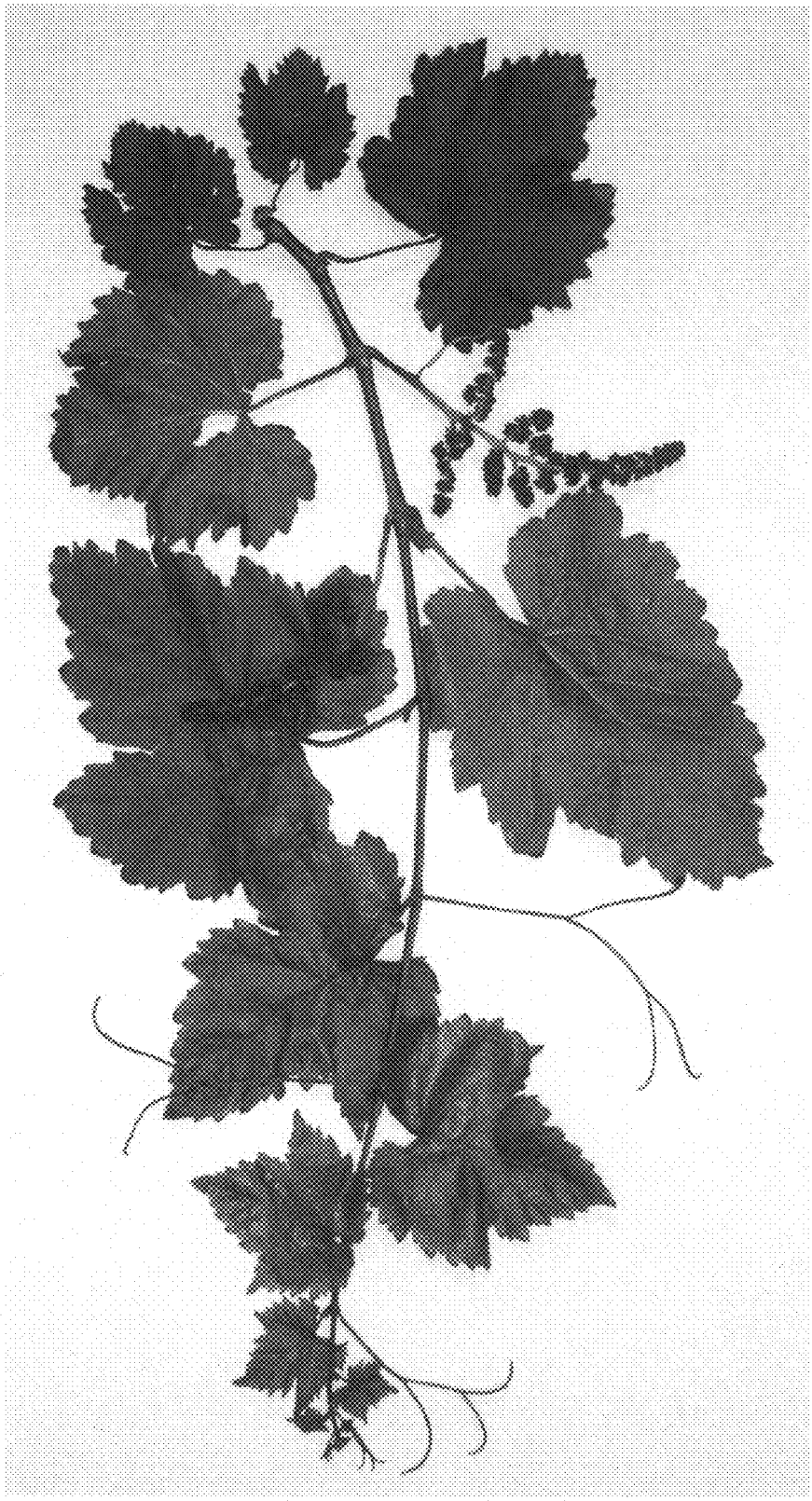
FIG. 1 shows a typical young vegetative shoot with attached floral clusters prior to anthesis.
Figure 2:
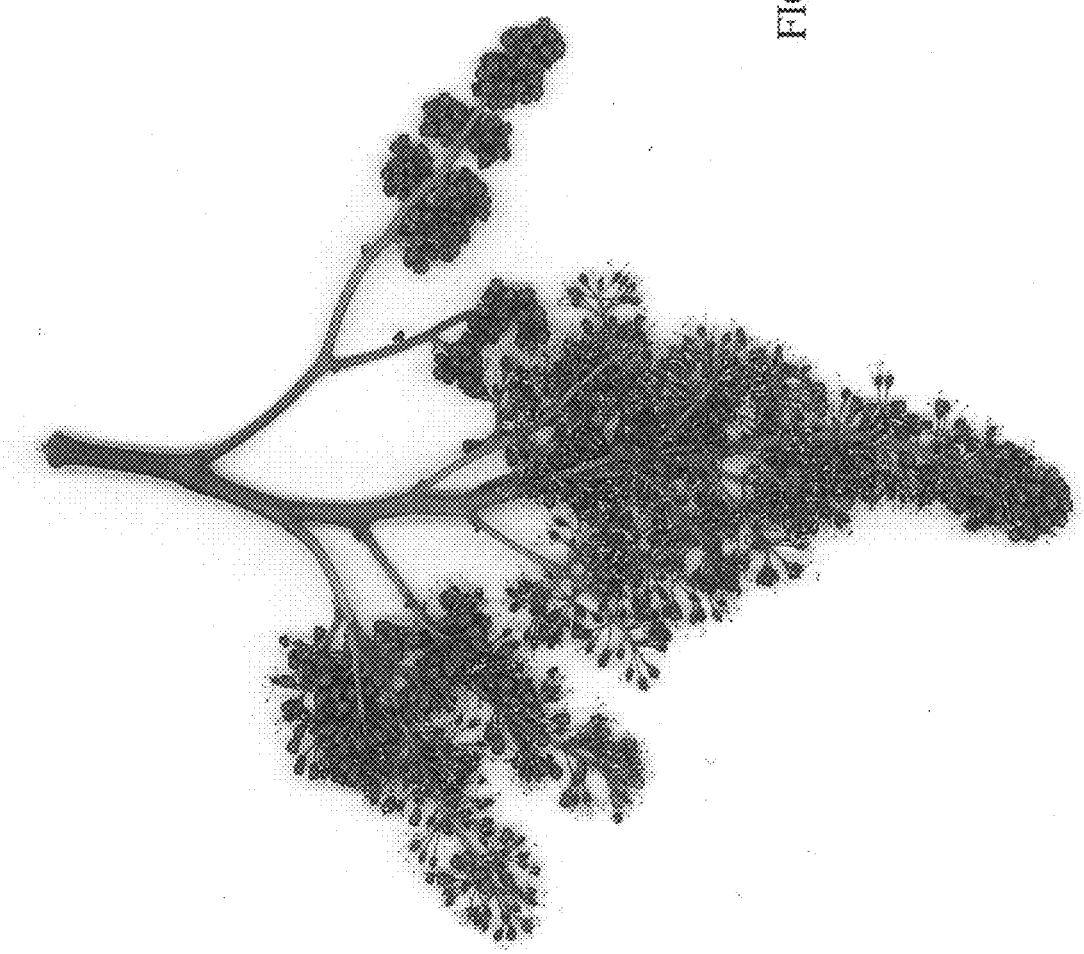
FIG. 2 shows the typical architecture of the present invention's flower cluster at approximately 50% bloom.

Description of the new invention applies to vines of 'Sunpreme' grown on its own roots at a density of approximately 1,119 vines per hectare in Fresno County, Calif. in 2012/2013.

The new variety cv. 'Sunpreme' may be distinguished from other commercial grape by a combination of characteristics, but particularly by its medium-sized green-colored seedless berries that begin to wilt naturally during mid-July in the San Joaquin Valley of Central California. The noted berry wilting is the first step in raisining, after which berries begin to brown naturally on the vine. The dried grapes (raisins) of this new variety are produced on strong woody canes that do not need to be cut from the mother vine to facilitate berry drying.

Referring more specifically to the botanical details of this new and distinct variety of grapevine, the following has been observed under the ecological conditions prevailing at the vineyard located in Parlier in the San Joaquin Valley of Central California. All major color code designations are by reference to the *Dictionary of Color*, by Maerz and Paul, First Edition, 1930. Common color names are also occasionally employed. Where dimensions, sizes, colors and other characteristics are given, it is to be understood that such characteristics are approximations of averages set forth as accurately as practicable. The description hereof was taken from specimens grown in Parlier, Calif. The grapevines used for measurement were grown in a fine sandy loam soil and the grapevines were irrigated using trickle, or drip irrigation. In a substantial part, the data presented here were from grapevines that were six years old.

Vine:

*Size*.—Medium. Grapevine size as determined by grapevines growing on a single cross arm 'T' trellis with the top cross arm approximately 91 cm long set approximately 142 cm above the ground. There were two wires on the cross arm and the grapevine was trained to produce a cordon height of approximately 147 cm and a spread of approximately 244 cm.

*Vigor*.—Medium vigor.

*Regularity of bearing*.—Regular. Annual pruning is required for reliable production.

Canes:

*Mature canes—diameter—internode base*.—Approximately 10.9 mm.

*Mature canes—diameter—internode midpoint*.—Approximately 7.8 mm.

*Mature canes—diameter—internode tip*.—Approximately 4.3 mm.

*Mature canes—diameter—node base*.—Approximately 12.3 mm.

*Mature canes—diameter—node midpoint*.—Approximately 10.1 mm.

*Mature canes—diameter—node tip*.—Approximately 6.5 mm.

*Internode length—base*.—Approximately 5.3 cm.

*Internode length—midpoint*.—Approximately 11.2 cm.

*Internode length—tip*.—Approximately 7.7 cm.

*Average length of canes*.—Approximately 146.5 cm.

*Surface texture*.—Striate.

*Color of mature cane*.—Plate 12 D7 Bran.

Buds:

*Bud color*.—Plate 13 K12.

*Bud texture*.—Smooth.

*Dormant bud* (*compound bud or eye*).—Width — Approximately 4.9 mm.

*Date of bud break*.—About Feb. 26, 2012. (early season).

Shoots:

*Young shoots*.—Tip form. Fully open, with glabrous stems and petioles.

*Density of prostrate hairs on shoot tip*.—Absent or very sparse.

*Anthocyanin coloration of shoot tip*.—Absent or very weak.

*Diameter of young shoots in spring* (*measured when shoots are approximately* 12 *inches in length*).—At approximately 5 cm above base, approximately 6.7 mm, at midpoint, approximately 4.8 mm, and at tip, approximately 2.4 mm.

*Internode length*.—Approximately 6.0 cm at 4th internode from base.

*Young shoots—color*.—Predominantly Plate 20 L6, with slight reddish tint upon direct sun exposure Plate 7 C5 sultana.

*Interstem of shoot tip—color*.—Green plate 20 L7 with no red streaks on the sun exposed side.

*Shoot shape*.—Erect prior to tying.

*Shoot tip*.—Form — Fully open.

Tendrils:

*Tendril size—length*.—Approximately 16.3 cm.

*Tendril size—diameter*.—Approximately 2.2 mm.

*Tendril shape*.—Most typical are un-branched, although bifurcate and trifurcate tendrils are observed. Tendrils are typically curled on distal end.

*Tendril pattern*.—The first tendril is typically found opposite node 6 or 7 from shoot base, with a second tendril opposite the next distal node. A tendril is then usually absent at the next node, and the pattern then repeats (tendril, tendril, blank) to the distal end of the cane.

*Tendril color*.—Sun-exposed side, Plate 6 J9 Rose Ash Devon, shade side, Plate 21 L4.

Leaves:

*Size*.—Leaves simple and alternate. The mid vein L1 is approximately 15.7 cm long, vein L2 is approximately 12.8 cm long and vein L3 is approximately 9.2 cm long. The angle between the mid vein L1 and L3 is approximately 103 degrees and between L1 and the 1st vein off L3 is approximately 148 degrees.

*Average length*.—Approximately 21.0 cm.

*Average width*.—Approximately 18.6 cm.

*Shape*.—Orbicular.

*Lobe number*.—Approximately Five (5).

*Color—upwardly disposed surface*.—Plate 23 H10.

*Color—downwardly disposed surface*.—Plate 22 J8.

*Leaf vein—color*.—Plate 17 F2.

*Leaf vein—thickness*.—Thickness of mid vein at center of leaf is approximately 1.3 mm.

*Density of erect hairs on main leaf veins*.—Absent or very sparse.

*Density of prostrate hairs between leaf veins*.—Absent or very sparse.
*Leaf margin*.—Serrated with shape of teeth both sides convex and medium in size.
*Petiole sinus*.—Slightly open to half open on mature leaves. Tooth at petiole sinus is absent. On mature leaf, sinus is approximately 3.6 cm deep and approximately 1.5 cm wide at widest point.
*Petiole length*.—Approximately 12.5 cm.
*Petiole diameter*.—Approximately 3.4 mm.
*Petiole color*.—Plate 21 J6 Mignon Green with very slight and occasional reddish pigment in the sun.
*Young leaf—color—upper surface*.—Plate 21 L8.
*Young leaf—color—lower surface*.—Plate 20 J7.
*Young leaf—shape unfolded*.—Concave.
*Stipules*.—Small and onion skin.

Trunk:
*Size*.—Medium.
*Size—height*.—Trunk splits for beginnings of cordons at approximately 91 cm above the ground level.
*Size—diameter*.—Approximately 8.4 cm as measured just below the cordon or head point at approximately 91 cm above vineyard floor; and approximately 7.3 cm at approximately 15.2 cm above the vineyard floor.
*Bark*.—Color — Plate 7 A1.

Flowers:
*Flower size*.—Medium.
*Flower unopened—diameter*.—Approximately 2.4 mm.
*Flower unopened—length*.—Approximately 3.6 mm.
*Flower unopened—surface texture*.—Smooth.
*Date of bloom*.—First bloom about Apr. 30, 2012.
*Date of full bloom*.—About May 8, 2012.
*Inflorescence*.—Panicle.
*Cluster size*.—At Bloom — Generally, medium.
*Cluster length*.—Approximately 19.8 cm.
*Cluster width*.—Approximately 22.2 cm.
*Peduncle length at bloom*.—Approximately 2.5 cm.
*Shape of cluster*.—Conical with well-developed shoulders.
*Calyptra color*.—Plate 20 L8.
*Stamens*.—Five (5) and erect.
*Pistil*.—Well developed.
*Ovary color*.—Plate 21 J10.
*Pollen*.—Normal, fertile, abundant.
*Anthers*.—Color — Plate 9 C1.

Fruit:
*Maturity when described*.—Ripe, firm fruit prior to any onset of berry wilting, typically mid-July in the San Joaquin Valley of Central California.
*Cluster size*.—Approximately 184 grams.
*Cluster length*.—Approximately 24.2 cm.
*Cluster width*.—Approximately 25.4 cm.
*Cluster shape*.—Conical.
*Cluster density*.—Medium, on average has approximately 145 berries per cluster.
*Clusters per vine*.—Approximately 117.
*Clusters per shoot*.—Approximately 2.25 clusters per shoot.

Peduncle:
*Size—length*.—Approximately 3.3 cm.
*Size—diameter*.—Medium, approximately 4.9 mm.
*Color*.—Plate 21 L6 (Parrot green).
*Texture*.—Smooth, glabrous.

Pedicel:
*Size—length*.—Approximately 8.1 mm.
*Size—diameter*.—Approximately 3.02 mm.
*Color*.—Plate 21 K5 Biscay green.
*Texture*.—Glabrous with a few brown lenticels.
*Brush*.—Length — approximately 1.96 mm.
*Brush color*.—Plate 17 D2.
*Attachment with berry*.—Good attachment.

Berry:
*Size*.—Approximately 2.34 grams.
*Shape*.—Obtuse-ovate.
*Length*.—Approximately 1.52 cm.
*Width*.—Approximately 1.34 cm.
*Color*.—Plate 19 K3 Chrysolite green.
*Bloom*.—Medium.

Skin:
*Thickness*.—Medium in thickness.
*Texture*.—Smooth.
*Tendency to crack*.—None.

Figure 3:
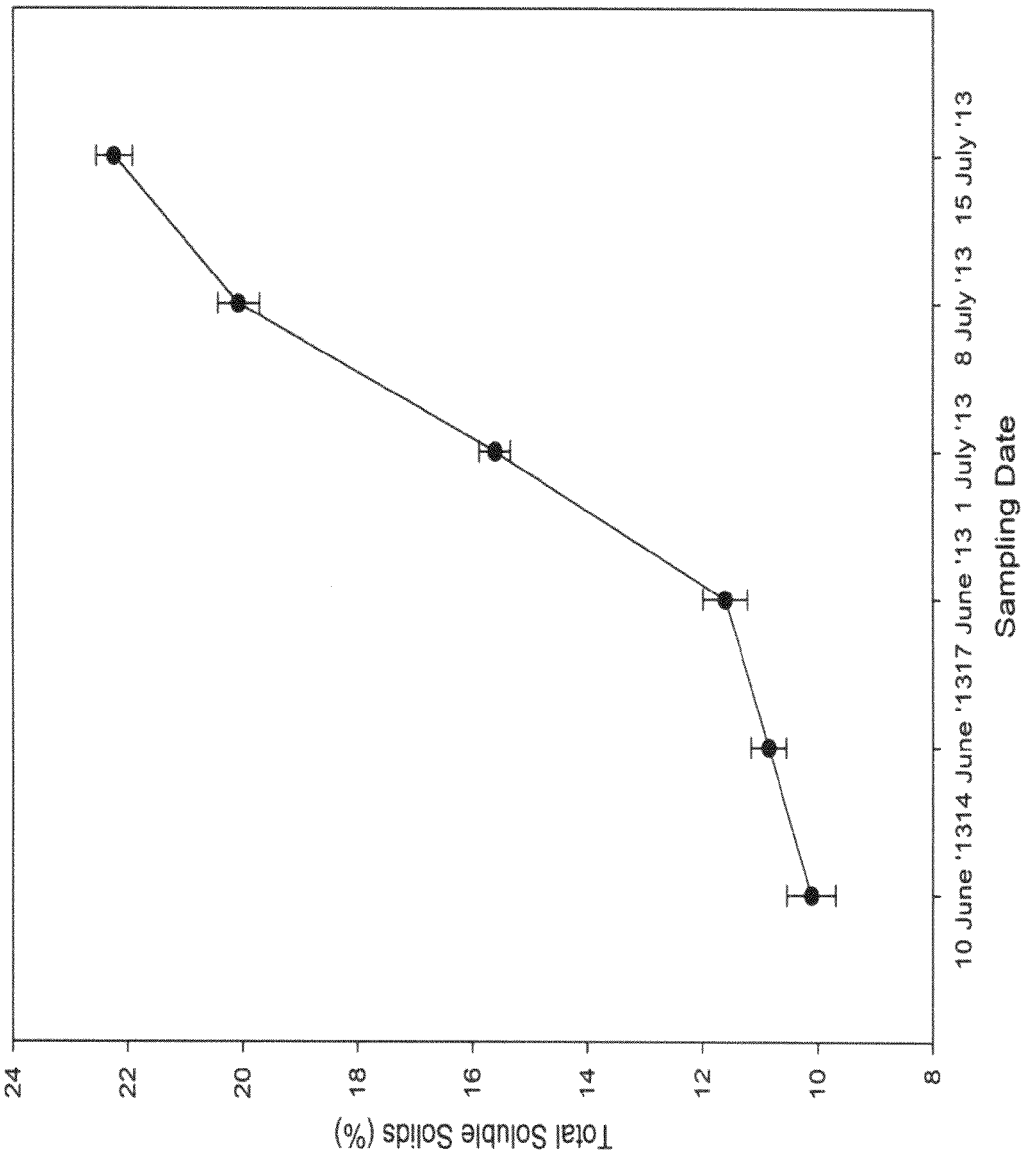
FIG. 3 is a graph showing the level of total soluble solids (Brix) presented as a function of time from berry verasion until the beginning of berry wilt.
Figure 4:
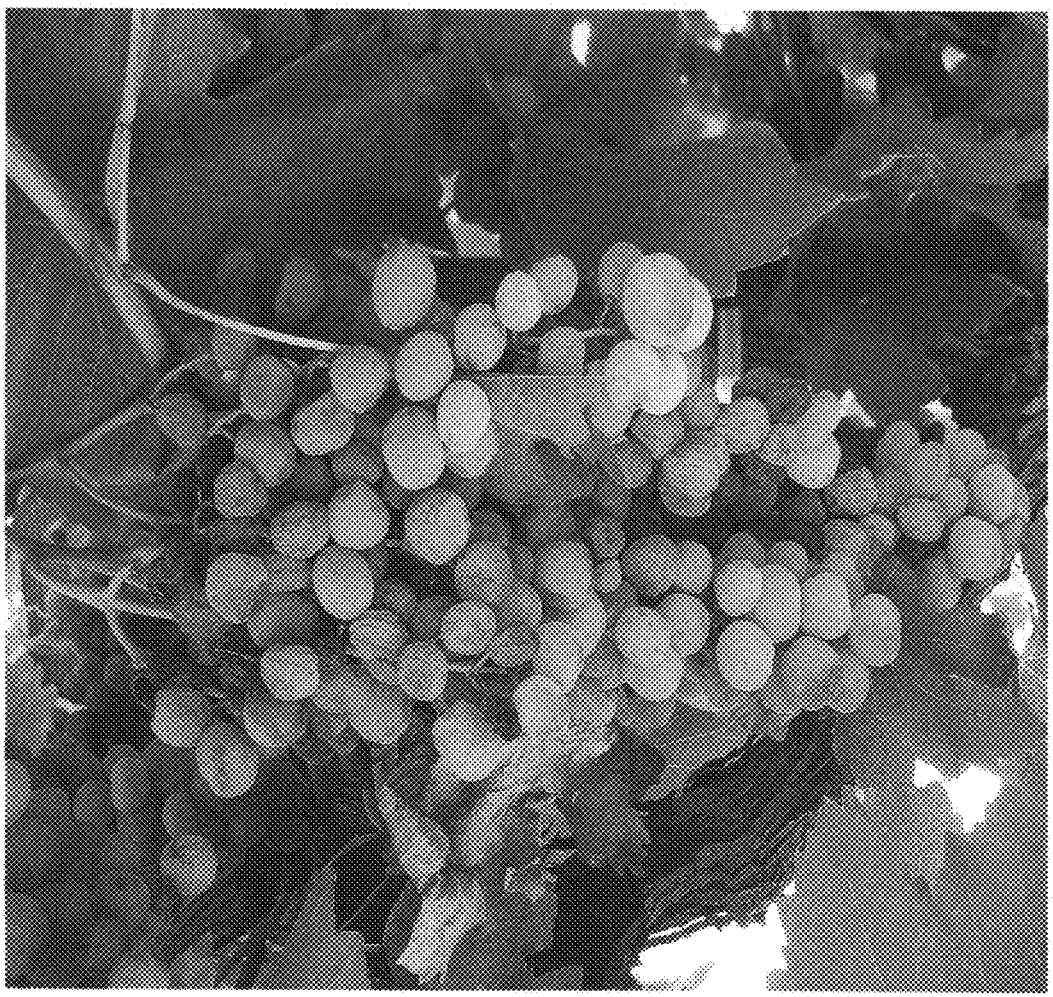
FIG. 4 shows a typical berry cluster at the onset of berry wilt.
Figure 5:
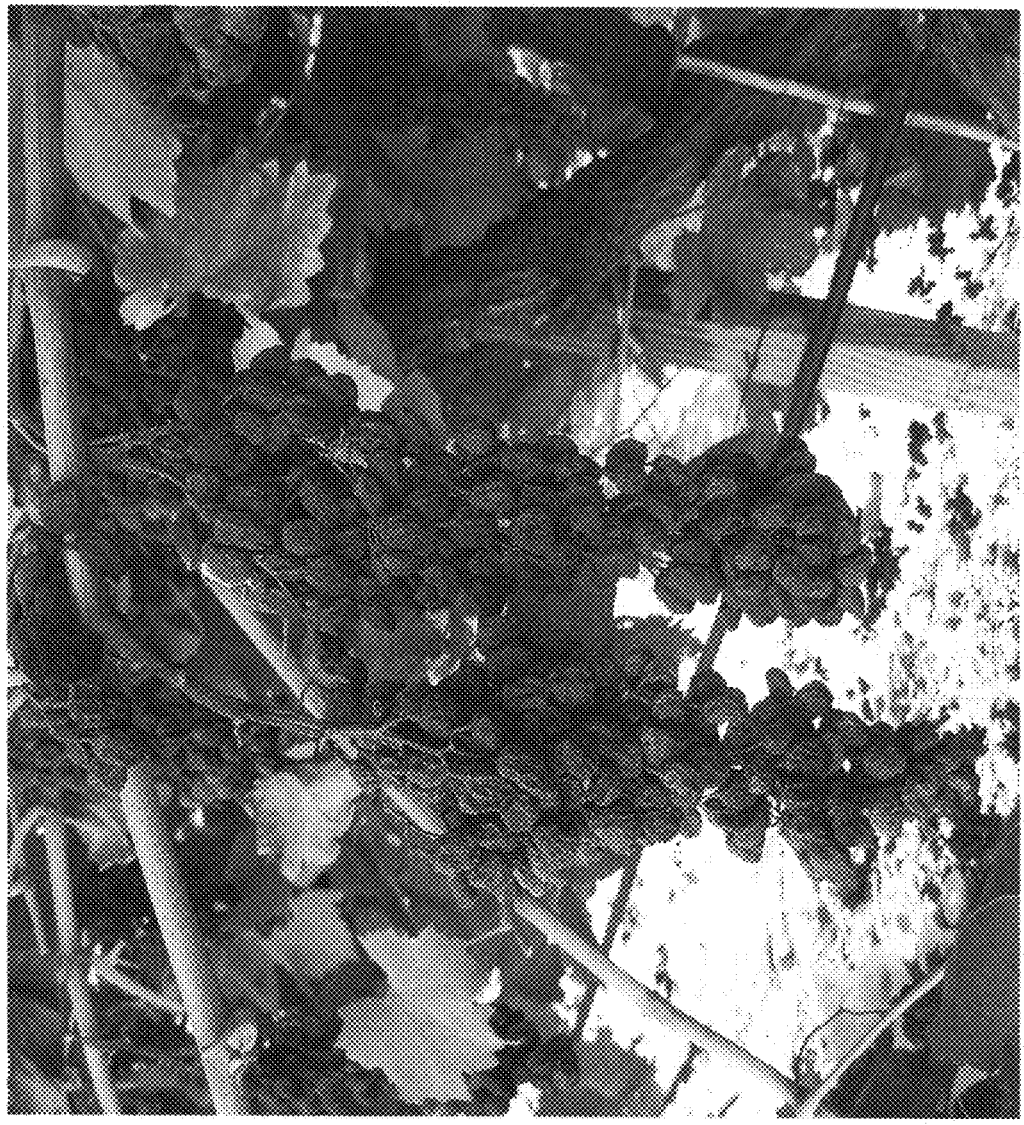
FIG. 5 shows dry clusters of raisins ready for harvest, attached to canes having turgid leaves. Canes have not been cut from the vine to effect berry drying.

Flesh:
*Flesh color*.—Plate 17 E2.
*Texture*.—Firm, meaty.
*Juice production*.—Medium.
*Color of juice*.—Clear.
*Flavor*.—Sweet and neutral flavor. Slight muscat flavor in very ripe fruit exposed to light.
*Soluble solids*.—Soluble solids content varies with fruit maturity. A representative profile of soluble solid content from berry verasion until the onset of berry wilting is provided in FIG. 3.
*Aroma*.—None.
*Ripening*.—Uniform.
*Eating quality*.—Good, sweet, slightly fruity with slight muscat flavor.

Dry product:
*Maturity when described*.—Dried berries (raisins) with an average moisture content less than 13%.
*Raisin length*.—Approximately 13.8 mm.
*Raisin diameter*.—Approximately 9.3 mm.
*Raisin mass*.—Approximately 0.70 g.
*Raisin color*.—Plate 8 J8 Java brown.
*Raisin flavor*.—Slightly fruity.
*Dry cluster length*.—Approximately 22.8 cm.
*Dry cluster mass*.—Approximately 91.8 g.

Disease resistance: Susceptible to powdery mildew, and fungicides were applied to the grapevines under evaluation to control powdery mildew.

Insect resistance: Insecticides were applied to the grapevines under evaluation to control general insect pests. No resistances to these pests were determined in these evaluations due to chemical control of these pests.

Character of seeds: Stenospermocarpic seedless, averaging 3.4 small aborted seed traces per berry that are not noticeable when eaten. Average aborted seed trace size when present is 5.6 mg fresh weight. Aborted seed color is Plate 22 L4 Calla green.

Use: For the production of raisins. No wine or fresh table grape evaluations have been performed to determine the new variety's suitability for these uses.

Keeping quality: Keeps well. Storage characteristics are similar to other raisins.

Shipping and handling qualities: Raisins of the present invention handle similar to 'Thompson Seedless' when it is dried as a raisin.

Raisin yield: At a vine density of approximately 605 vines per acre, mature vines have yielded an average of approximately 4.4 tons/acre, with raisin quality averaging approximately 89% B or better grade.

Tolerance of environmental extremes: The vine has been grown exclusively in Fresno County, Calif., and has not been subjected to extreme winter temperatures. As a *Vitis vinifera* variety, winter hardiness would be limited. 'Sunpreme' is expected to perform similarly to other *V. vinifera* varieties with respect to response to low winter tempertures. Drought and heat tolerance of the new variety have not been specifically tested. However, 'Sunpreme' has been grown under irrigation successfully since 2001, enduring high summer temperatures prevalent in the San Joaquin Valley without any signs of damage from heat or drought.

Although the new variety of grapevine possesses the described characteristics noted above as a result of the growing conditions prevailing in Fresno, Calif. in the Central San Joaquin Valley of California, United States of America, it is to be understood that variations of the usual magnitude and characteristics incident to changes in growing conditions, training, irrigation, fertilization, pruning, pest control, climatic variation and the like are to be expected.

We claim:

1. A new and distinct variety of grapevine substantially as illustrated and described, characterized by its ability to dry berries naturally without the aid of cane cutting, and thereby produce high quality raisins on vines that can also be spur pruned.

* * * * *